United States Patent [19] [11] 4,383,529
Webster [45] May 17, 1983

[54] IONTOPHORETIC ELECTRODE DEVICE, METHOD AND GEL INSERT

[75] Inventor: Henry L. Webster, Providence, Utah
[73] Assignee: Wescor, Inc., Logan, Utah
[21] Appl. No.: 202,889
[22] Filed: Nov. 3, 1980
[51] Int. Cl.³ .............................................. A61N 1/30
[52] U.S. Cl. ........................................ 604/20; 128/802
[58] Field of Search .................. 128/207.21, 639–641, 128/644, 783, 798, 802, 803, 156, 268

[56] References Cited

U.S. PATENT DOCUMENTS

| | | | |
|---|---|---|---|
| 542,508 | 7/1895 | Van Tuyl, Jr. | 128/207.21 |
| 568,095 | 9/1896 | Muir | 128/798 |
| 2,555,037 | 5/1951 | Jensen | 128/803 |
| 3,659,614 | 5/1972 | Jankelson | 128/803 X |
| 3,882,853 | 5/1975 | Gofman et al. | 128/641 |
| 3,989,036 | 11/1976 | Sasamori | 128/640 |
| 3,998,215 | 12/1976 | Anderson | 128/641 |
| 4,109,648 | 8/1978 | Larke et al. | 128/639 |
| 4,141,359 | 2/1979 | Jacobsen et al. | 128/207.21 |
| 4,230,105 | 10/1980 | Herwood | 128/156 |

FOREIGN PATENT DOCUMENTS 1965195  7/1971  Fed. Rep. of Germany ...... 128/640

Primary Examiner—Lee S. Cohen
Attorney, Agent, or Firm—Mallinckrodt & Mallinckrodt

[57] ABSTRACT

An iontophoretic electrode device, method, and hydrophilic, hydrated gel insert for the electrode device all involve a preformed, shape-retaining, gel body preferably of disc formation having mutually opposite, parallel faces. An agar gel disc having an ionic drug diffused throughout is the preferred, iontophoretic gel body that is packaged and sold as such for insertion in a cup-like receptacle and securement to an electrode plate within the receptacle, so as to protrude free and clear therefrom for pressing against the skin of a medical patient.

16 Claims, 4 Drawing Figures

IONTOPHORETIC ELECTRODE DEVICE, METHOD AND GEL INSERT

BACKGROUND OF THE INVENTION

1. Field

The invention is in the field of electrode devices for use in the iontophoretic transporting of drug molecules through the skin.

2. State of the Art

The use of iontophoresis to transport a drug in solution through intact skin is well known. It is based on the principle that ions in solution will migrate in the presence of an electrical potential. Iontophoresis is performed by placing an electrode containing an ionic drug source onto the skin through which the drug is to be transported. A second electrode is placed on the skin near the first electrode and voltage is applied sufficient to cause current to pass through the skin between the electrodes. The ionic drug molecules migrate toward the second electrode and are thus transported through intact skin. A particular use of this technique is in the administration of pilocarpine nitrate or chloride to stimulate sweat gland secretion in a localized area of the skin.

In the past, electrode devices used as a drug source in iontophoretic applications have included a drug-soaked pad made of gauze, layers of filter paper, or some other absorbent fabric material. Drug-soaked pads are disadvantageous, however, because pressure on the pad, such as occurs during electrode attachment, forces drug solution out of the pad. Moreover, drug-soaked pads are prone to evaporation. Either of these occurrences leads to an insufficient amount of drug solution in the pad, which exposes the patient to the danger of electrical burns and also makes the amount of drug actually transported through the skin unpredictable. In an attempt to provide a sufficient source of drug ions and to protect against burns, it has been necessary to periodically add drug solution to the drug-soaked pad; but if too much drug solution is added, excess solution may spill onto the skin where it offers a low-resistance path for current to flow across the skin surface, thereby reducing the amount of drug transported through the skin.

Improved versions of the above are shown in Jacobsen et al. U.S. Pat. Nos. 4,141,359 and 4,166,457, and a prefilled disposable unit is shown in Reeves U.S. Pat. No. 3,677,268.

An application of iontophoresis in dentistry is disclosed in U.S. Pat. No. 3,215,139 to V. H. Dietz, who employs sodium alginate as a gel substrate for fluoride ions to be iontophoretically applied to a patient's teeth. Sodium alginate is soluble in water. It and the fluoride are mixed with water to form a sticky, impressionable composition which is allowed to gel around the teeth following application by means of the patient biting into an open receptacle containing the composition. Gelation takes about two or three minutes and the "gel" formed is a heterogeneous, gummy substance, rather than a solid, clear, homogeneous gel. Dietz suggests that other vegetable gums such as gum tragacanth or agar-agar might possibly be substituted for the sodium alginate, although he notes that agar-agar is not very desirable because of the heat involved in its use. Actually, agar-agar, also spoken of merely as agar, is not soluble in water except at elevated temperatures. It could not be satisfactorily employed in the manner disclosed by Dietz.

U.S. Pat. No. 3,989,050 teaches the use of various gels of a mayonnaise-like consistency as conducting materials for application to metallic plate electrodes used for long-time monitoring purposes. It does not indicate whether or not these gels can be used in iontophoretic applications.

Agar has long been used to prepare solid media for culturing microorganisms. When mixed with the nutrient broth at the common rate of 1.5 to 2.0% (w/v), the agar forms a fibrous structure which is fine enough to prevent motility of bacteria within it but coarse enough to permit diffusion of nutrients.

SUMMARY OF THE INVENTION

According to the present invention, an electrode device for use in the iontophoretic transporting of an ionic drug through intact skin is constructed so as to incorporate therein a hydrophilic, hydrated gas as a semi-solid, shaped retaining, replaceable body of disc or other suitable shape which can be easily handled and packaged as such and inserted in a corresponding receiving recess of, or otherwise attached to, an electrode device. The gel shape contains the drug and the electrolyte and serves in place of the drug-soaked pad or the sticky, on-the-job-mixed mass used in previous electrode devices. Agar gel is a preferred hydrophilic, hydrated gel for the purpose. An anti-fungal substance may be and preferably is added to insure against fungal growth during storage.

Use of an easily handled and packaged, drug-containing, gel disc or the like in place of a drug-soaked, absorbent pad or sticky mass avoids many problems. Inasmuch as the gel disc is essentially solid and shape retaining, there is no leakage of electrolyte even when substantial pressure is applied. Furthermore, the gel disc retains the necessary electrolyte and drug in a predetermined and reproducible concentration.

In practice, the electrode device incorporating the gel body which contains the drug and the electrolyte is secured over the portion of skin through which the drug is desired to be transported. A second electrode device, which is preferably the same as the first but incorporates a gel disc or other suitable shape that contains electrolyte but no drug, is secured over the skin at an appropriate location relative to the drug-containing electrode device. In activating sweat glands by the application of pilocarpine, the second electrode device is placed on the skin adjacent to the first electrode device. A voltage is applied to the two electrodes such that current passes between then, thus causing the drug ions to migrate through a localized portion of the skin of a patient from the first electrode toward the second.

THE DRAWING

In the accompanying drawing, which represents the best mode presently contemplated for carrying out the invention:

FIG. 1 is a full face view showing the working face of the electrode device of the invention;

FIG. 2, a corresponding view showing the opposite face;

FIG. 3, a longitudinal vertical section taken along the line 3—3 of FIG. 1 and drawn to a larger scale; and FIG. 4, a view in perspective of the gel disc insert.

DETAILED DESCRIPTION OF THE ILLUSTRATED EMBODIMENT

Figure 1:
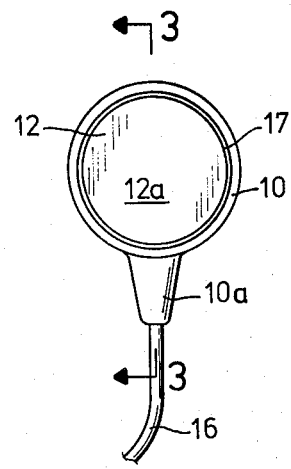
Figure 2:
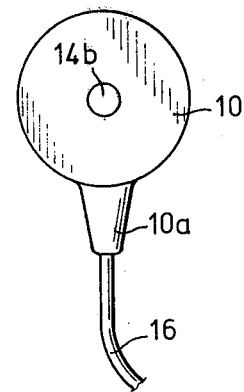
Figure 3:
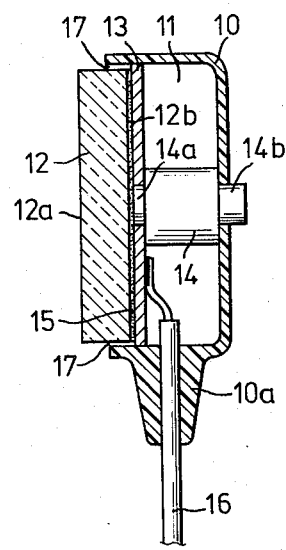
Figure 4:
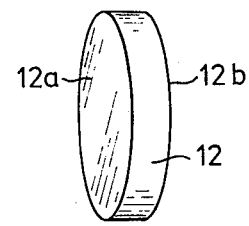

As shown in the drawing, the electrode device of the invention comprises electrode structure in the form of a cup-like receptable 10 of electrically non-conductive material, such as a thermoplastic molded to shape, providing an open recess 11 adapted to receive a formed, substantially solid body 12 of a hydrophilic, hydrated gel performed as a disc having mutually opposite and parallel, flat faces 12a and 12b.

An electrically conductive plate 13 is positioned within receptable 10 for supporting disc 12 so that its skin-contacting face 12a is free and clear of the walls of the receptacle by at least enough to make good electrical contact with the skin against which the electrode device is placed. As illustrated, plate 13 is secured in place on a centrally disposed, supporting pin 14, also of electrically non-conductive plastic material and having an end portion 14a which fits tightly, as by a press fit, in a central receiving opening of plate 13 and an opposite, longer, end portion 14b which extends tightly, again as by a press fit, through a corresponding central opening in the closed bottom of receptacle 10. Pin portion 14b provides the customary anchorage for a securement stap (not shown) commonly used to fasten an electrode device in place on the arm or other appropriate part of the body of a patient. A viscous, electrically conductive material 15, such as mucilage, is applied to the exposed face of plate 13 prior to inserting gel disc 12, so as to secure such disc in good electrically conductive relationship with the plate.

An insulated electrical conductor 16 extends into recess 11 of receptacle 10 below plate 13 through a boss member 10a of such receptacle and is electrically connected to plate 13, as by soldering. Conductor 16 is connected by any suitable means, such as a plug connection (not shown), to a source of electrical voltage whose polarity will depend upon whether the electrode device is one for the iontophoretic administration of a drug, such as pilocarpine nitrate or chloride, or a back-up electrode for use therewith.

Hydrophilic, hydrated gel disc 12 is preferably formed from agar, although a protein, e.g. collagen, gel or a synthetic polymer, e.g. methyl cellulose, gel may also be used for the purpose. In any event, the gel body is performed to the desired disc or other suitable shape so as to be substantially solid and shape-retaining during use. For the iontophoretic administration of a drug, the gel body is prepared with the ionic drug additive added to the gel material so that, on gelation, it is diffused throughout the body. For the back-up electrode, no drug is added to the gel material.

A hydrophilic, hydrated gel contains an electrolyte as part of its normal make-up and is electrically conductive. When the gel material is used in appropriate concentration, the resulting gel is semi-solid so that it retains its structure yet allows free movement of drug molecules within. A gel body so made has a low rate of water evaporation from its surfaces, and does not lose fluid nor its shape under the pressures applied during use.

It has been found that agar discs are sufficiently solid for use in iontophoresis when the agar concentration is about 3% (w/v) or somewhat in excess thereof. The preferred concentration is about 4% (w/v) although higher concentration may be used so long as sufficient electrolyte to be effective is present.

A typical agar gel disc used for the iontophoretic application of a pilocarpine salt is made by adding 4 grams of powdered agar, 0.5 grams of pilocarpine nitrate or chloride, 0.2 grams of methyl paraben and 0.1 gram of propyl paraben to 100 mls of cold water. The paraben derivatives are anti-fungal compounds. This mixture is heated to boiling until the solids are completely dissolved, after which the solution is allowed to stand for about one hour at approximately 70° C. in order to allow air bubbles to leave the solution. Next, the hot liquid is poured into a flat-bottomed tray to a depth of about 0.5 cm and allowed to cool. After the solution has cooled, the resultant semi-solid gel is conveniently cut into discs with a tube having one end sharpened as a cutter. The prepared discs are sealed in plastic bags or similar containers and stored under refrigeration.

Alternatively, the hot liquid could be poured into suitable molds before cooling.

When a physician is ready to administer a drug, he will insert a disc 12 having the proper drug incorporated therein into the recess 11 of the receptacle 10 of the electrode device, having first smeared electrode plate 13 with mucilage 15 or a material similar to that disclosed in U.S. Pat. No. 3,989,050. The gel disc is pressed onto the material 15 and rotated slightly with light pressure to expel any entrapped air. The transparent nature of the disc facilitates inspection for air bubbles. The material 15 provides a stable, uniform, air-free attachment bed for the gel disc and holds the disc firmly in place.

It is not necessary that the disc 12 fit tightly into receptacle 10. On the contrary, it is preferred that a slight gap 17 exist between the disc and the walls of recess 11 to better facilitate insertion of the disc and the removal of air bubbles from beween the disc and the viscous conducting material 15.

For use, the free and unconfined gel face 12a of the electrode device is placed flat against the patient's skin over an area to be treated. The device is held in place by the customary strap (not shown) which passes around the applicable portion of the patient's body and is provided with an eyelet through which the projecting end 14b of pin 14 fits. Projection of gel face 12a beyond the walls of recess 11, even though slight, ensures good electrical contact with the skin. The gel disc is ordinarily about 5 millimeters thick and preferably projects beyond receptacle 10 by about half its thickness.

A second electrode device, which is preferably similar to the first but having a gel disc 12 without drag, is similarly secured onto the skin near the first, and both electrode devices are electrically connected to a voltage source sufficient to cause current to flow through the skin between the electrodes. If the drug is cationic, as is pilocarpine nitrate or chloride, the drug-containing electrode device is connected to the positive terminal of the voltage source and the second electrode is connected to the negative terminal. Since the ionic form of a pilocarpine as nitrate or chloride carries a positive charge, it will migrate toward the negative electrode. If a anionic, i.e. negatively charged, drug is employed, it will migrate toward the positive electrode, thus requiring the drug-containing electrode device to be connected to the negative terminal of the voltage source.

When the voltage is applied, current will flow through the skin between the electrodes. An ionic drug molecule migrates toward the oppositely charged electrode, and thereby passes through intact skin. The extent of migration of drug ions through the localized portion of a patient's skin lying between the electrodes is dependent upon both the current intensity and the duration of current application.

Iontophoresis is routinely used for diagnosing cystic fibrosis. Pilocarpine is administered in order to induce sweating, the sweat being collected and analyzed. A current flow of about 2.0 milliamperes applied for about 10 minutes has been found sufficient for this application. Although iontophoresis is often employed for administering other substances at current levels of up to about 6 milliamperes, current flow at this level becomes uncomfortable for many people.

Whereas this invention is here illustrated and described with specific reference to an embodiment thereof presently contemplated as the best mode of carrying out such invention in actual practice, is to be understood that various changes may be made in adapting the invention to different embodiments without departing from the broader inventive concepts disclosed herein and comprehended by the claims that follow. For example, other shapes than the preferred disc may be employed so long as provision is made for good electrical contact of the gel with both the electrode element and the skin of the patient, and other than a cup-like receptacle can be employed as the electrode structure so long as it holds the gel shape with its working face extending sufficiently free and clear of such structure to make the required good electrical contact with the skin of a patient.

I claim:

1. An iontophoretic electrode device, comprising an electrode adapted for electrical connection to a voltage source; and a preformed, shape and fluid retaining, semisolid body of a hydrophilic, hydrated gel throughout which is diffused an ionic drug for administration to a patient through intact skin by iontophoresis, said body being secured to the electrode in good electrical contact therewith and having a free and unconfined, solid gel contact face so disposed as to make good electrical contact with the skin of a patent when the electrode device is applied to the patient.

2. An electrode device according to claim 1, wherein the gel is an agar gel.

3. An electrode device according to claim 4, wherein the agar gel has an agar concentration of no less than about 3% (w/v) or greater.

4. An electrode according to claim 5, wherein the agar concentration is about 4% (w/v).

5. An electrode device according to claim 1, wherein the gel body is conductively secured to the electrode by means of a thin layer of a viscous, electrically conductive material.

6. An electrode device according to claim 1, wherein the gel body is a flat disc having mutually opposite, parallel faces.

7. A method of transporting ionic drug molecules through the skin of a medical patient by means of iontophoresis, comprising pressing against an area of skin through which the drug is to be transported a free and unconfined, solid gel contact face of a shape and fluid retaining, semi-solid, hydrophilic, hydrated gel body which has the ionic drug molecules diffused throughout and which is secured in good electrical contact to an electrode, so said body can serve as an iontophoretic electrode; applying a second iontophoretic electrode to the patient; and electrically energizing said electrodes by electrical power of respectively different polarities to effect the desired transporting of said ionic drug molecules through said area of the skin.

8. For use as a drug-administering insert in an iontophoretic electrode device, a performed, shape and fluid retaining, semi-solid body of a hydrophilic, hydrated gel having an ionic drug diffused throughout and having a free and unconfined, solid gel contact face.

9. A drug-administering insert according to claim 8, wherein the body is of flat disc formation having mutually opposite, parallel faces.

10. A semi-solid gel body in accordance with claim 8, wherein the gel is an aqueous agar gel having an agar concentration of about 4% w/v.

11. A substantially solid gel body in accordance with claim 10, wherein the ionic drug is pilocarpine for iontophoretic use in the stimulation of human sweat glands for the determination of cystic fibrosis.

12. An iontophoretic electrode device for administering an ionic drug by iontophoresis to a medical patient, comprising a rigid, cup-like receptacle of electrically non-conductive material having a rimmed opening for the reception of a substantially conforming, preformed, shape and fluid retaining, semi-solid body of a hydrophilic, hydrated gel containing the ionic drug to be administered; an electrode plate spaced inwardly of said receptacle from said rimmed opening; and an electrical conductor adapted for connection with a source of electrical power and extending into electrical connection with said electrode plate; a preformed, shape and fluid retaining, semi-solid body of drug-containing, hydrophilic, hydrated gel substantially conforming to and secured within said opening by adherence to said electrode plate, the thickness of said semi-solid body being such as to protrude slightly from said receptacle beyond said rimmed opening so as to present a free and unconfined, solid gel face of said body for contact with the skin of a medical patient, whereby, under iontophoresis, the drug will pass into the body of the patient without leaving foreign matter on the skin so contacted; and securement means for holding the receptacle on the body of the patient with said solid gel face in contact with the patient's skin.

13. An iontophoretic electrode device in accordance with claim 12, wherein the electrode plate is spaced from the bottom of the receptacle to provide a space within which the electrical conductor extends and connects to said electrode plate.

14. An iontophoretic electrode device in accordance with claim 13, wherein a non-conductive pin has end portions tightly fitted into respective receiving openings in the bottom of the receptacle and in the electrode plate, respectively, the end portion of the pin received by the bottom of the receptacle projecting outwardly from said bottom to provide the securement means whereby the receptacle can be held on the body of the patient.

15. An iontophoretic electrode device in accordance with claim 12, wherein the drug to be administered is pilocarpine for inducing sweating at the area of skin contacted by the gel.

16. An electrode device according to claim 12, wherein the gel body is conductively secured to the electrode plate by means of a thin layer of a viscous, electrically conductive material.

* * * * *